United States Patent [19]

Kleesattel

[11] 4,281,987
[45] Aug. 4, 1981

[54] ULTRASONICALLY DRIVEN LOW-SPEED ROTARY MOTOR

[75] Inventor: Claus Kleesattel, Rego Park, N.Y.

[73] Assignee: Cavitron Corporation, New York, N.Y.

[21] Appl. No.: 113,983

[22] Filed: Jan. 21, 1980

[51] Int. Cl.$^3$ .............................................. A61C 1/07
[52] U.S. Cl. .................................. 433/103; 433/119; 433/125; 51/59.55; 310/26; 318/118; 74/155; 74/126
[58] Field of Search ............... 433/119, 125, 105, 103, 433/114; 51/59.55, DIG. 11; 310/26; 318/118; 128/24 A; 74/155, 88, 111, 126, 128

[56] References Cited

U.S. PATENT DOCUMENTS

| Re. 25,033 | 8/1961 | Balamuth et al. | 51/59.55 |
|---|---|---|---|
| 2,774,193 | 12/1956 | Thatcher et al. | 51/59.55 |
| 2,838,137 | 6/1958 | Wallerstein et al. | 74/126 |
| 2,874,470 | 2/1959 | Richards | 310/26 |
| 2,990,616 | 7/1961 | Balamuth et al. | 51/59.55 |
| 3,058,218 | 10/1962 | Kleesattel et al. | 433/119 |
| 3,139,543 | 6/1964 | Balamuth et al. | 51/317 |
| 3,204,133 | 8/1965 | Tschudin | 310/26 |
| 3,254,402 | 6/1966 | Balamuth et al. | 228/110 |
| 3,419,776 | 12/1968 | Kleesattel et al. | 318/118 |

OTHER PUBLICATIONS

"Bonding with Torsional Mode Vibration," Christensen, Western Electric Tech. DIG. No. 4, 10-1966, pp. 25, 26.

Primary Examiner—Gene Mancene
Assistant Examiner—John J. Wilson
Attorney, Agent, or Firm—R. M. Skolnik; W. R. Evans

[57] ABSTRACT

A device using longitudinal ultrasonic vibrations for rotating a shaft at relatively low rotational speeds is particularly useful for rotating a brush-type tooth polisher on an insert for an ultrasonic dental prophylaxis unit. The device has a sleeve which supports the rotatable shaft and a vibrator. A disc is normal to the axis of rotation of the shaft and connected to the shaft for rotation. A transducer at one end of the vibrator responds to excitation for producing longitudinal ultrasonic vibrations in the vibrator, and the other end of the vibrator which is urged against the disc with a constant force converts the longitudinal vibrations into elliptical motion to engage one face of the disc during an arc of the elliptical motion. This imparts substantially only pulses of tangential driving force and normal vibrational forces to rotate the disc and shaft unidirectionally. In one preferred embodiment, the vibrator has a single driving pad urged against the disc. In another, it is forked and has two contact pads (points) to engage the disc alternately on opposite sides of the shaft during opposite directions of the tangential elliptical motion for improved efficiency. In still another, the vibrator is bifurcated to engage opposed faces of the disc simultaneously to cancel the static loading forces acting on the disc whereby bearing wear is virtually eliminated.

11 Claims, 8 Drawing Figures

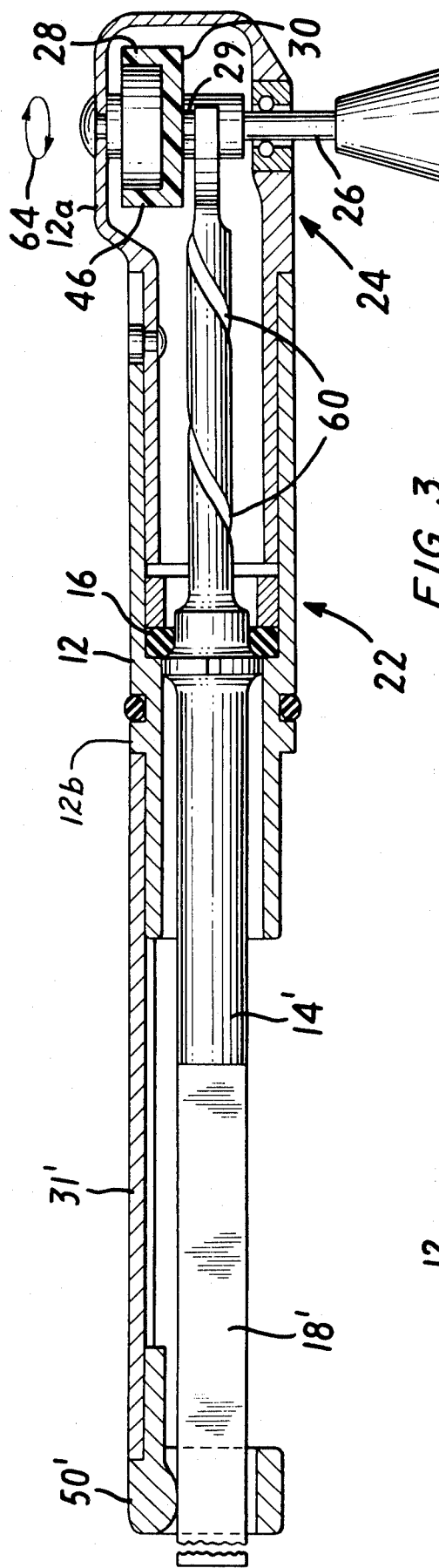
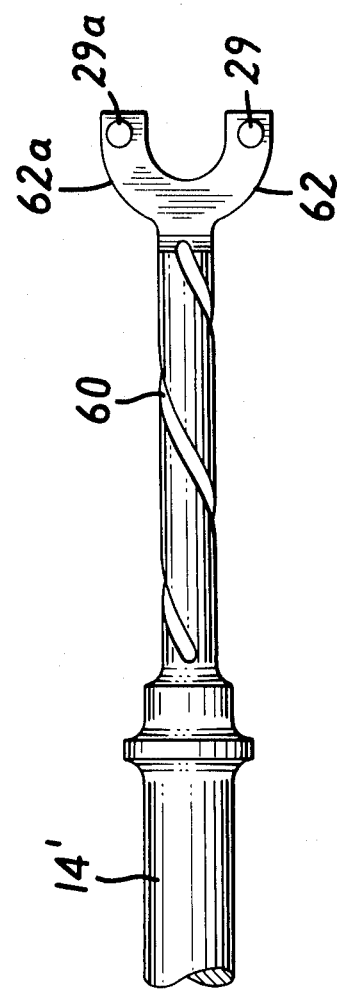
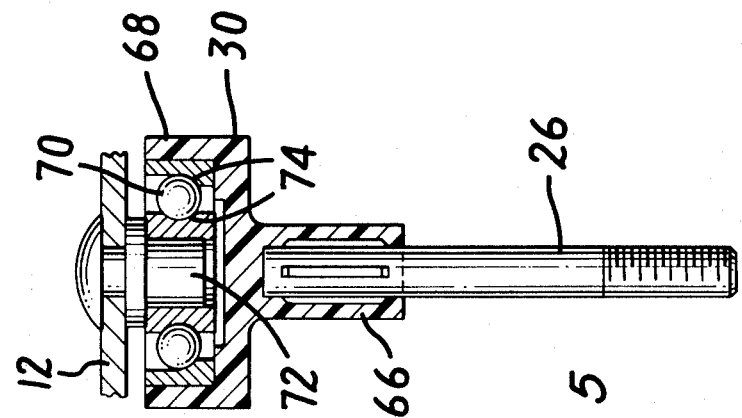
FIG. 3
FIG. 4
FIG. 5

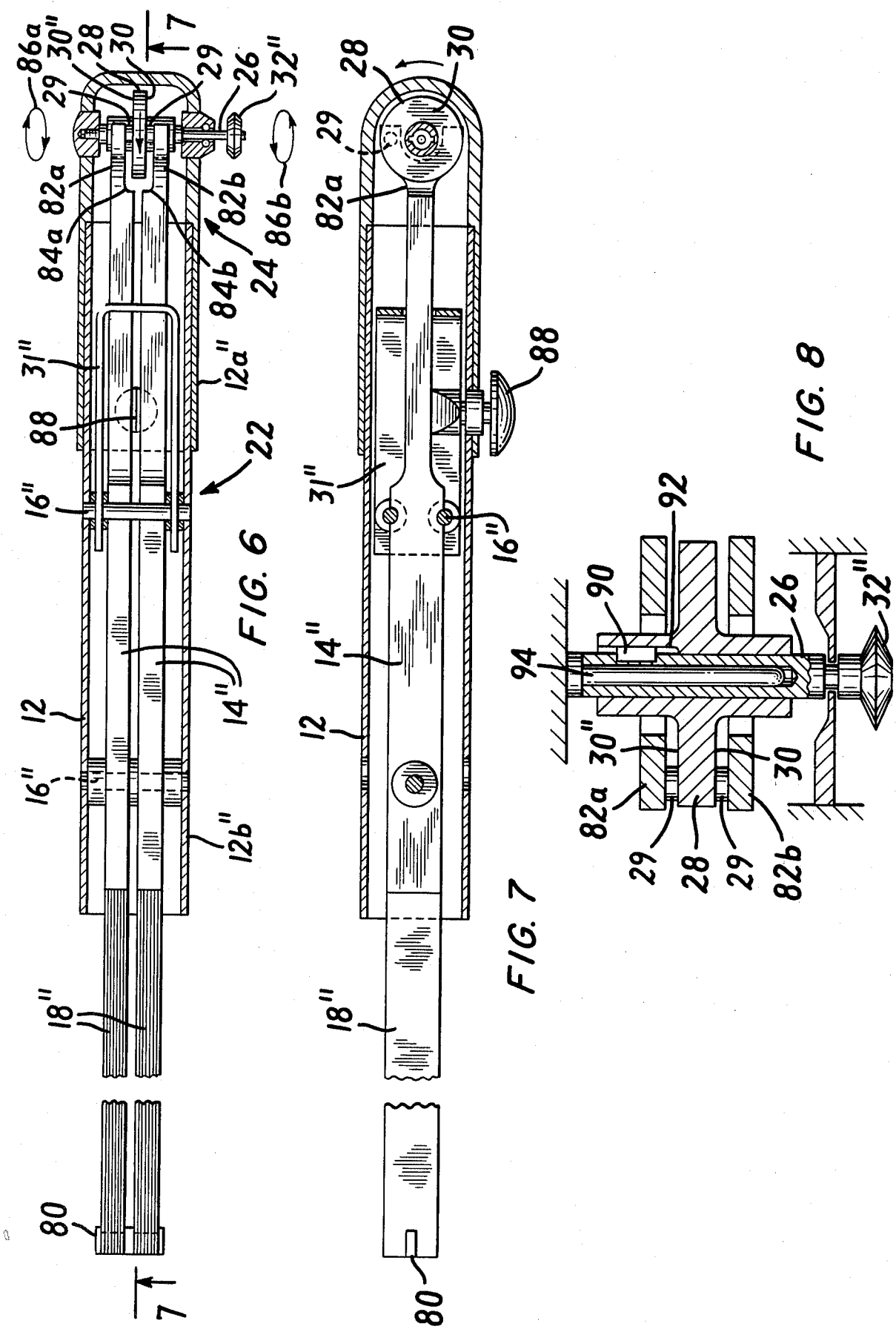

ULTRASONICALLY DRIVEN LOW-SPEED ROTARY MOTOR

BACKGROUND OF THE INVENTION

This invention relates to an ultrasonically-driven rotary device and, more particularly, a rotary dental polisher device.

One of the most widely accepted new dental instruments of recent years is the ultrasonic dental prophylaxis device. Such devices have a power unit which converts AC line-frequency electrical power into higher frequencies and a flexible cable which carries the higher frequency power to a hand held, tubular housing. An insert for the device has a sleeve for releasably connecting the insert to the housing and for supporting a vibrator. One end of the vibrator projects into the housing and is a magnetostrictive or other transducer device responsive to the higher frequency electrical excitation means in the housing for producing longitudinal ultrasonic vibrations in the vibrator. The other end of the vibrator is the dental tool. The two ends of the vibrator are usually connected by a connecting body which, by a reduction in diameter or change in acoustic impedance, amplifies the ultrasonic vibrations at the tool. The whole vibrator is also an integral multiple of one-half the wavelength of the ultrasonic vibrations in the vibrator to be resonant for maximum vibration and to have at least one node of ultrasonic vibration. The sleeve is usually arranged to support the vibrator at the node to avoid damping the vibrations.

The tool end of the vibrator has at least one bend which converts the longitudinal ultrasonic vibrations in the vibrator into ultrasonic elliptical motion at the tool end as described in the assignee's U.S. Pat. No. 2,990,616. The elliptical motion of the tool is there used to dislodge ultrasonically calculus, plaque and other matter adhered to teeth, particularly along the gum line. Removing calculus and plaque from teeth by hand is well known for the periodontal and hygienic treatment of teeth, and the ultrasonic dental prophylaxis unit provides similar treatment with the improvement and assistance of ultrasonic vibrations, in the way of a power tool.

In addition to removing calculus and plaque, however, teeth often require polishing or abrasive brushing to remove stains and otherwise clean broader areas of the teeth more rapidly. Such polishing is generally accomplished with a relatively low-speed rotary rubber cup or brush and a polishing compound. Periodontists and hygienists have thus required two pieces of equipment, the ultrasonic dental prophylaxis device and a rotary polisher.

Rotary polishers have, until now, generally been driven by dental drilling equipment, but another recent innovation in dentistry presents its own, further problem for the relatively low speed rotary polishing of teeth. This innovation is the high speed air turbine dental drill. Its very high rotational speeds on the order of $10^5$ rpm are desirable for dental drilling, but greatly in excess of the rotational speeds suitable for the rotary brushing or polishing of teeth. One limitation on the speeds of such rotary polishing, for example, is retaining the polishing compound on the rotating brush. For this, rotational speeds on the order of $10^2$ to $10^3$ rpm are desired. If the new air turbine drive is thus to be used for rotary polishing, an expensive speed reduction gear must be provided to achieve the much lower rotary polishing speeds.

Alternatively, the old-fashioned, variable-speed, electrical belt-driven dental drilling apparatus may be used, but such devices with their large, multi-arm belt structures are particulary intimidating to many patients. In addition, three pieces of equipment and two power supplies are then required for a full dental operatory: the electric ultrasonic prophylaxis unit for removing tartar, the high speed turbine drill and air power supply for drilling of teeth, and the electric belt-driven unit for polishing.

There has thus been for some years a desire to consolidate the various functions both for economic and aspectual advantage. This desire, however, has so far led only to suggestions of combining the rotary drilling and polishing functions with the disadvantages just described, or to combining the ultrasonic prophylaxis and high-speed rotary drilling functions as described in the assignee's U.S. Pat. No. 3,058,218.

This patent discloses a way of rotating a drill at high speeds with longitudinal ultrasonic vibrations. The longitudinal ultrasonic vibrations are produced at a transducer end of a resonant vibrator in an insert connected to a housing and converted into elliptical motion at the other end of the vibrator in the same way as described for the ultrasonic prophylaxis device. The elliptically-moving end of the vibrator under pressure tangentially engages a shaft which is rotatably mounted in or adjacent the vibrator during one arc of the ellipse. The high frequency of the ultrasonic vibrations, generally in a range of from 15 to 50 kHz, however, rotates the shaft at correspondingly high speeds of from 45,000 to 360,000 rpm in the examples in the patent. Such speeds are greatly in excess of those suitable for rotary polishing at least because the polishing compound cannot be retained on the polisher. Thus, even though the patent initially suggests using the ultrasonically driven rotary device for "abrading and polishing operations" such operations must be considered grinding-type polishing and not the brushing-type polishing for cleaning teeth considered here. This is further confirmed by the patent's consistent emphasis of high rotational speeds, as opposed to the low speeds desired for polishing.

The patent also discloses only rotating the drill shaft directly from the elliptically moving end of the vibrator. As the elliptical motions under pressure tangentially engage the shaft during one arc of the ellipse to rotate the shaft unidirectionally, they impart also high-frequency impacts to the shaft. In addition to that, the rotating polisher-tool shaft or drill has some axial thrust applied to it. It has been found difficult, at least economically, to provide a bearing for a directly rotated element or elements as disclosed in the patent which will withstand for longer periods of time these radial and axial forces in the environment of ultrasonic vibrations.

SUMMARY OF THE INVENTION

It is therefore an object of the invention to provide a single device suitable for both ultrasonic dental prophylaxis treatment and the relatively low speed rotary polishing of teeth.

It is further an object of the invention to provide a device which uses longitudinal ultrasonic vibrations for rotating a shaft which may carry a polisher at relatively low rotational speeds.

It is still further an object of the invention to provide an ultrasonic vibrator torsionally responsive to the ultrasonic vibrations therein.

To these ends, the invention provides a device which uses longitudinal ultrasonic vibrations for rotating a shaft at relatively low rotational speeds. A vibrator in the device has a longitudinal vibration-producing transducer end and an opposite end which converts the longitudinal vibrations into elliptical motion (which as used herein includes circular and other loop motions). The shaft to be rotated carries a disc normal to the shaft and connected to the shaft for rotating it. The elliptically moving end of the vibrator engages under pressure a face of the disc tangentially to a concentric circle on the face of the disc during an arc of the elliptical motion to rotate the disc unidirectionally. Substantially only tangential driving force pulses, axial vibratory impacts plus a constant axial loading force are thus provided to the shaft.

In one preferred embodiment, the polisher shaft bearing is a ball race between the face of the disc opposite that engaged by the vibrator and a support. In this embodiment, therefore, the disc is part of the motor and part of the bearing.

In another preferred embodiment, the vibrator is forked for engaging the disc face on opposite sides of the shaft with the opposite tines of the fork in response to a vibration-responsive torsion arrangement which is also part of the vibrator. The vibrator thus rotates the disc during both directions of motion tangential to the disc.

Still another preferred embodiment has a bifurcated vibrator which straddles the disc to engage simultaneously opposed (upper and lower) faces of the disc on the same side of the shaft with the tangential driving arc of the elliptical motion of each vibrator portion. This provides a unique advantage; although the tangential components of the elliptical motion are in the same direction to rotate the disc unidirectionally, the axial motion components and the constant loading forces are opposite and thus tend to cancel both the axial impacts and the static contact force to relieve the bearing load.

The several features of the invention and its various preferred embodiments thus provide a practical way of combining an ultrasonic dental prophylaxis device and a low speed rotary polisher. The combination in this merely preferred use therefore eliminates one piece of equipment and, possibly, an auxiliary air power supply formerly required to equip a dental operatory, all as contemplated in the objects of the invention. These and still other features of the invention are further described in connection with the various preferred embodiments.

DESCRIPTION OF THE DRAWINGS

Preferred embodiments which are intended to illustrate but not to limit the invention will now be described with reference to drawings in which:

FIG. 3 is an enlarged elevation of another preferred embodiment, partly in section;

FIG. 4 is a plan view of a portion of the embodiment shown in FIG. 3;

FIG. 5 is a still further enlarged elevation of another portion of the embodiment shown in FIG. 3, partly in section;

FIG. 6 is an enlarged elevation of another preferred embodiment, partly in section;

FIG. 7 is a bottom view of a portion of the embodiment shown in FIG. 6, partly in section; and FIG. 8 is a still further enlarged elevation of another portion of the embodiment shown in FIG. 6, partly in section.

DESCRIPTION OF THE PREFERRED EMBODIMENTS

Figure 1:
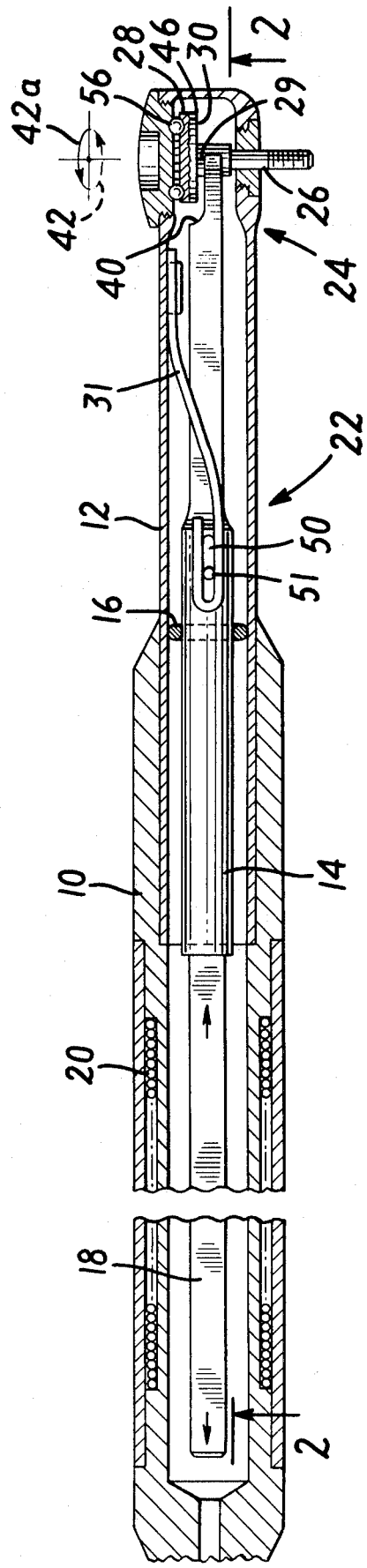
FIG. 1 is an enlarged elevation of one preferred embodiment, partly in section.

Each of the preferred embodiments, which are most completely shown in FIGS. 1, 3 and 6, is an insert for the tubular, hand-held housing 10 (FIG. 1) of the previously described ultrasonic dental prophylaxis device. Each insert has a sleeve 12 which supports the insert on the housing. The sleeve 12 also supports a vibrator 14 (FIG. 1), 14' (FIG. 3) or 14" (FIG. 6) of the insert with one or more resilient rings 16 or pins 16" (FIG. 6) between the sleeve and vibrator. Each vibrator has a magnetostrictive transducer end portion 18 (FIG. 1), 18' (FIG. 3) or 18" (FIG. 6) which is responsive to a vibration-exciting arrangement (energizing coil 20 in FIG. 1) in the housing 10 (FIG. 1) for producing longitudinal ultrasonic vibrations in the vibrator; a connecting body portion at 22 for transmitting the longitudinal vibrations with or without amplitude magnification; and a driving tip end portion at 24 which is shaped to add at least one other vibration component to the original longitudinal one for converting the longitudinal ultrasonic vibrations into elliptical ultrasonic motion.

In each of the preferred embodiments (FIGS. 1, 3 and 6), the sleeve 12 supports a rotatable shaft 26 which extends transversely to the vibrator adjacent the driving tip 24. A disc 28 is concentrically mounted on the shaft normal to the shaft. A point (contact pad) 29 affixed to the adjacent driving tip of each of the vibrators 14, 14' and 14" engages, under pressure, at least one disc face 30, 30" (FIG. 6) with one component of its elliptic motion tangential to a concentric circle on the disc face for rotating the disc unidirectionally by making contact with the disc face only during an arc of each cycle of the elliptic motion. This generates a unidirectional torque on the disc to make it rotate.

In addition to the tangential, rotation-driving engagement between the points 29 on the driving tips and the discs, each preferred embodiment also has a spring 31 (FIG. 1), 31' (FIG. 3) or 31" (FIG. 6) which presses the respective points 29 against the disc faces 30, 30" with a static force. The static force provides sufficient friction-engagement between the points and discs to rotate the discs with the tangential component of the elliptic motion.

Each of the preferred embodiments is thus characterized by a similar friction-drive arrangement for rotating a disc 28 with its shaft 26 through the longitudinal ultrasonic vibrations excited in the vibrator. The disc, particularly, distinguishes the structure from the assignee's beforementioned U.S. Pat. No. 3,058,218 in which the vibrating tip directly rotates a small-diameter shaft. This difference implies two important consequences. Firstly, the thrusts both static and dynamic caused by the forces normal to the disc face are axial to the shaft, rather than radial to the shaft as in the patent. The axial vibrations are more easily accommodated by the bearings supporting the shaft, particularly when the disc itself provides a bearing surface of increased size (FIG. 1), and may even be canceled by simultaneously engaging opposing disc faces with bifurcated vibrator portions (FIG. 6). Secondly, engaging a disc-shaped rotor makes it possible to engage the driving radius farther away from the shaft to reduce the rotational speed, as opposed to the high rotational speed design of the patent, and provides greater torque.

Each preferred embodiment is illustrated for use with a polisher cup (not shown in FIG. 1 or 6, but 32' in FIG. 3) on an end of the shaft 26 which projects from the sleeve. With the reduced rotational speeds which the preferred embodiments can provide, a polishing compound will be retained on the polisher cup. The invention thus makes it possible to replace the tartar-removing scaler insert of a dental prophylaxis unit with the low-speed rotary polishing insert here described to combine the prophylaxis and rotary polishing functions of the separate devices heretofore used.

A FIRST PREFERRED EMBODIMENT

Particular features of a first preferred embodiment shown in FIGS. 1 and 2 can now be described. The driving tip at 24 of the vibrator 14 with its point (contact pad) 29 has a step 40 on the top, disc side of the vibrator 14. The step adds a transverse vibration component to the longitudinal vibration of the vibrator to produce the elliptical motion indicated by arrow 42. The tip bears a point 29 which is pressed against the disc face 30 by the action of the prestressed springs 31. The elliptical motion has a major axis parallel to the disc face 30 for tangentially driving the disc with a major component 42a of the elliptical motion, and preferably with the peak velocity of the tangential elliptical motion. This is accomplished when a 90° phase shift exists between the longitudinal and transverse motions.

The contact pad or point 29 is made from a material which is wear resistant in relation to a coating 46 on the disc surface 30. The high, ultrasonic frequency (15 to 50 KHz) of the successive driving engagements between the contact pad and disc, however, may still produce some wear both on the contact pad and disc as a consequence of the slippage that is taking place. Instead of, or in addition to making the disc-part of the insert replaceable to avoid the effects of such wear (as later explained), the disc may also be encased in a wear-resistant coating 46.

The springs 31 are a pair of wires on opposite sides of the vibrator. One end of each wire is connected to the sleeve 12 and the other end engages an elongated projection 50 on the side of pivotal support pins 51 toward the driving tip 24, the pins 51 being at or near a vibrational node in the vibrator to avoid damping the vibrations. The springs thus urge the point 29 on the driving tip upwardly toward the disc face 30 to provide and maintain static contact force (for example, about 10 Newtons) between the point 29 and disc face 30 as they wear.

Figure 2:
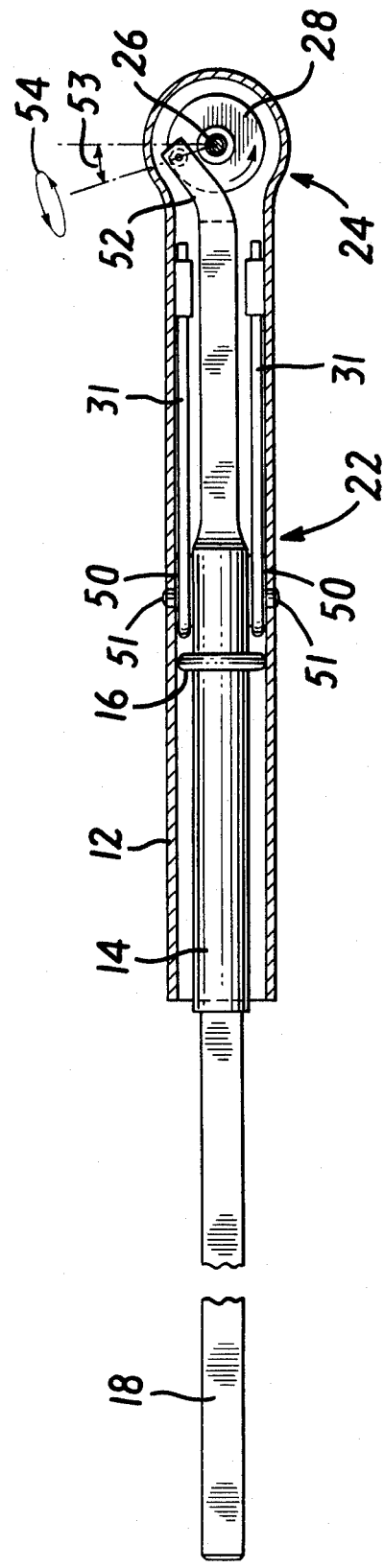
FIG. 2 is a bottom view of the preferred embodiment shown in FIG. 1, partly in section.

FIG. 2 more clearly shows that driving tip 24 of the vibrator has a further bend 52. This bend introduces a second elliptical component to the motion at the contact pad 29 as indicated by the arrow 54. FIG. 2 also shows that the contact pad engages the disc slightly leftward at an angle 53 to a diameter of the disc transverse to the longitudinal axis of the vibrator. The elliptical motion 54 thus makes the actual direction of the upper, driving arc 42a of the elliptical motion 42 (FIG. 1) correspond more closely to a tangent to a concentric circle on the disc. Maximum utilization of the tangential, rotation-driving contact with minimum slippage and friction losses between the disc and contact pad is thus achieved.

The bend 52 also offsets the contact pad 29 from the shaft at the disc center so that the shaft can be on the axis of the vibrator. This avoids torque on the vibrator and handpiece when pressure is applied to the shaft 26 in polishing use of the device.

A SECOND PREFERRED EMBODIMENT

A second preferred embodiment is shown in FIGS. 3, 4 and 5. As shown in FIG. 3, the vibrator 14' has a second node of ultrasonic vibration at the point of contact between the transducer 18' end and a pad 50', the other node being at the mounting ring 16. One end of a leaf spring 31' serves as a seat for the pad 50' which is mounted on the leaf spring 31' and the other end is connected to the sleeve 12. The leaf spring with its pad 50' urges the transducer 18' downwardly to pivot the vibrator on O-ring 16 and thus urge contact pads 29, 29a on the driving tip at 24 against the face 30 of disc 28 in similarity to the springs 31 described for the prior preferred embodiment. To put the subassembly mounted in housing portion 12a back in place in housing portion 12b, or remove it, pad 50' is merely urged upwardly.

The vibrator 14' also differs from that previously described in having at least one helical groove 60, which is right-handed from the node at rubber ring 16 as shown. The contact pads 29, 29a are respectively mounted on opposite tines 62, 62a of a fork at the driving tip. The tines straddle the shaft 26 so that the contact pads engage the disc on opposite sides of the shaft. The length, depth and pitch of the helical groove 60 is selected in relation to the stroke of the ultrasonic vibrations in the vibrator such that the groove torsionally rotates the vibrator in response to the longitudinal ultrasonic vibration, i.e. a phase-shifted lateral vibration is created, to engage the contact pads 29, 29a with the disc alternately during respective rightward and leftward vibrational strokes in such a manner that a unidirectional torque is generated. In combination with the longitudinal ultrasonic vibration, each of the tines thus moves elliptically, as shown by arrow 64 for tine 62, to rotate the disc, alternately, clockwise. The forked vibrator tines thus serve the double purpose of spacing the contact pads radially of the disc to reduce the speed and drivingly engaging the disc alternately on opposite sides of the shaft for greater power output than attainable with the single contact pad in the embodiment previously described.

The disc 30 again provides a large circumference ball bearing race for taking the static thrust and the ultrasonic impacts axial of the shaft. As shown in FIG. 5, however, the rotor assembly differs somewhat from that of FIG. 1. The shaft 26 is secured to a stud portion 66 of the disc 30. Peripheral wall portions 68 of the disc 30 project parallel to the shaft 26, to provide a space for an angular contact ball bearing 70. The bearing thus accommodates the static thrust produced by leaf spring 31' as well as the radial and axial thrusts which come from the polisher 32' when in use.

THIRD PREFERRED EMBODIMENT

FIGS. 6 and 7 show a third preferred embodiment in which the vibrator 14" is bifurcated remote from the driving tip. Specifically, the vibrator 14" is bifurcated from the end opposite the driving tip and joined there by a key 80 to equalize the vibration amplitudes of the two vibrator portions.

The ends 82a, 82b of the vibrator portions at the driving tip straddle opposed, upper and lower disc faces 30", 30. They have opposite, mirror image steps 84a, 84b which convert the longitudinal ultrasonic vibrations of the vibrator portions into elliptical motion indicated, respectively, by the arrows 86a, 86b. Each end 82a, 82b thus has a component of elliptical motion normal to the disc 28 which is 180° out of phase with the other. Each end 82a, 82b therefore engages the respective opposed surfaces 30", 30 of the disc 28 simultaneously for rotating the disc 28 counter-clockwise. The simultaneous engagement of the opposed disc faces 30", 30 tends to cancel not only the static loading forces but also the axial ultrasonic impacts on the disc so that the bearing requirements for supporting the shaft are substantially reduced. Because of the aforementioned force cancelation, a pin bearing 94 projecting into the shaft 26 is sufficient for rotationally supporting the shaft.

A leaf spring clip 31", as before, urges each end 82a, 82b of the driving tip against the disc 28 with a predetermined force. To put the subassembly 12a" back in place, or remove it, a tapered plunger 88 is pushed upward forcing apart the two vibrator portions.

FIG. 7 also shows that the vibration converting end 82a and the mirror-image vibration converting end 82b (FIG. 6) are forked in similarity to the embodiment shown in FIG. 4, but only provided with one contact pad 29 for engaging the disc with only one tine of the fork. It is thus readily apparent, however, that a further preferred embodiment (not shown) could combine the helical groove 60 of the embodiment shown in FIG. 4 with each of the bifurcated vibrator portions shown in FIG. 6 for alternately engaging opposite sides of the disc simultaneously on opposed faces of the disc. This would combine the bi-directional tangential drive advantage of the embodiment shown in FIG. 4 with the axial vibration-canceling advantage of the embodiment shown in FIG. 6. This and other combinations and variations of the several preferred embodiments are contemplated as being within the scope of the invention.

FIG. 8 shows a still further advantage of the bifurcated vibrator structure which simultaneously engages opposed faces 30, 30" of the disc 28 to cancel all forces normal to the disc faces. As shown in FIG. 8, the disc 28 is free to slide axially on the shaft 26 but is connected to the shaft for torque transmission by a key 90 projecting from the shaft 26 into a keyway or slot 92 in a stud portion of the disc. This allows the disc position on shaft 26 to adapt itself to the balanced position of the two vibrators 14".

I claim:

1. An insert for a device having housing means for exciting longitudinal ultrasonic vibrations, the insert comprising:
    a sleeve connectable to the housing means;
    a shaft rotatably supported on the sleeve;
    a disc normal to the shaft and connected to the shaft for rotation therewith;
    a vibrator supported in the sleeve, the vibrator having transducer means at one end responsive to the housing means for producing longitudinal ultrasonic vibrations in the vibrator, and having driving tip means at the other end for converting the longitudinal vibrations into elliptical motion and for engaging one face of the disc with the elliptical motion so as to impart to the disc substantially only torque-generating vibrational thrusts tangential of the disc for rotating the disc and vibrational thrusts normal to the disc; and
    means for urging the driving tip means against the disc with a static pressure.

2. An insert as in claim 1; and further comprising bearing means between the sleeve and the other, opposed face of the disc for distributing the vibrational thrusts normal to the disc.

3. An insert as in claim 2, wherein the bearing means comprises ball bearings annularly between the other, opposed disc face and the sleeve.

4. An insert as in claim 1 or 2, wherein the driving tip means comprise vibration-responsive torsion means in the vibrator for torsionally vibrating at least the driving tip end of the vibrator about the longitudinal axis of the vibrator in response to the longitudinal vibrations of the vibrator.

5. An insert as in claim 4, wherein the vibration responsive torsion means comprise a helical groove adjacent the driving tip means of sufficient length, depth and pitch to rotate the vibrator.

6. An insert as in claim 4, wherein the driving tip means comprises a fork having spaced apart tines on opposite sides of the shaft for tangentially engaging the disc with alternate tines during opposite directions of the longitudinal vibrations through the torsional vibration of the vibrator.

7. An insert as in claim 1, wherein the vibrator is longitudinally bifurcated at least at the driving tip means, each bifurcated vibrator portion having a driving tip means for simultaneously engaging opposed faces of the disc on the same side of the shaft with the elliptical motion of the driving tip means whereby the vibrational thrusts normal to the disc tend to cancel.

8. An insert as in claim 7; and further comprising linkage means for allowing the disc to move axially of the shaft while retaining the torque transmission therebetween.

9. An insert as in claim 8, wherein the linkage means comprise a keyway in one of the shaft and disc and a key in the other projecting into the keyway.

10. An insert as in claim 1, or 7; and further comprising at least one wear-resistant contact pad on the vibration converting means for engaging the disc.

11. An insert as in claim 1, 2, or 7, wherein the sleeve comprises two interfitting portions, one supporting the shaft and one supporting the vibrator for separating the shaft and disc from the vibrator.

* * * * *